(12) United States Patent
Sherman et al.

(10) Patent No.: US 7,052,497 B2
(45) Date of Patent: May 30, 2006

(54) TECHNIQUES FOR SPINAL SURGERY AND ATTACHING CONSTRUCTS TO VERTEBRAL ELEMENTS

(75) Inventors: Michael C. Sherman, Memphis, TN (US); Fred J. Molz, IV, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 357 days.

(21) Appl. No.: 10/219,029

(22) Filed: Aug. 14, 2002

(65) Prior Publication Data

US 2004/0034351 A1 Feb. 19, 2004

(51) Int. Cl.
*A61B 17/70* (2006.01)

(52) U.S. Cl. ....................................................... 606/61
(58) Field of Classification Search .................. 606/61, 606/60, 72, 74, 59, 103, 105
See application file for complete search history.

(56) References Cited

U.S. PATENT DOCUMENTS

| 4,934,935 | A | * | 6/1990 | Edwards ..................... 433/174 |
|---|---|---|---|---|
| 5,041,139 | A | | 8/1991 | Branemark |
| 5,246,370 | A | | 9/1993 | Coatoam |
| 5,370,697 | A | * | 12/1994 | Baumgartner ............ 623/17.15 |
| 5,387,213 | A | | 2/1995 | Breard et al. |
| 5,520,687 | A | | 5/1996 | Howland |
| 5,769,852 | A | | 6/1998 | Branemark |
| 5,868,745 | A | | 2/1999 | Alleyne |
| 6,083,522 | A | | 7/2000 | Chu et al. |
| 6,190,388 | B1 | | 2/2001 | Michelson et al. |
| 6,248,106 | B1 | | 6/2001 | Ferree |
| 6,280,474 | B1 | | 8/2001 | Cassidy et al. |

FOREIGN PATENT DOCUMENTS

| EP | 0 498 709 | | 2/1992 |
|---|---|---|---|
| FR | 2 662 073 | A1 | 11/1991 |
| WO | WO 01/45576 | A1 | 6/2001 |

* cited by examiner

*Primary Examiner*—Eduardo C. Robert
*Assistant Examiner*—David Comstock
(74) *Attorney, Agent, or Firm*—Krieg DeVault LLP

(57) ABSTRACT

Techniques for spinal surgery include accessing at least one vertebral element of the spinal column. At least one loading member is engaged to the at least one vertebral element. The loading member is allowed to integrate with the bony structure of the vertebral element over time. The integrated loading member is accessed in a second surgical procedure, and can be loaded and/or attached to a construct.

43 Claims, 6 Drawing Sheets

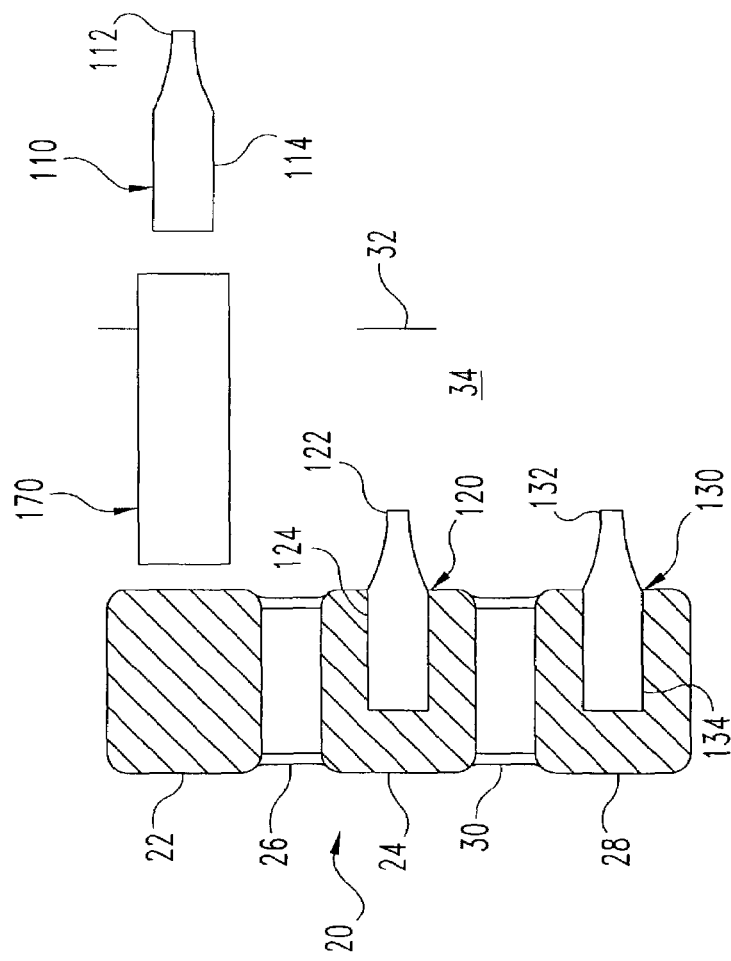
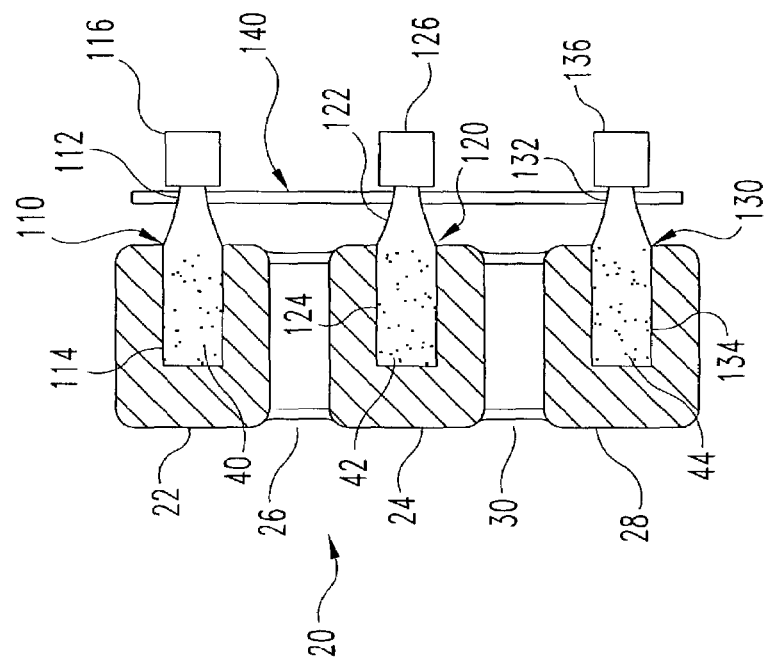
Fig. 5
Fig. 6

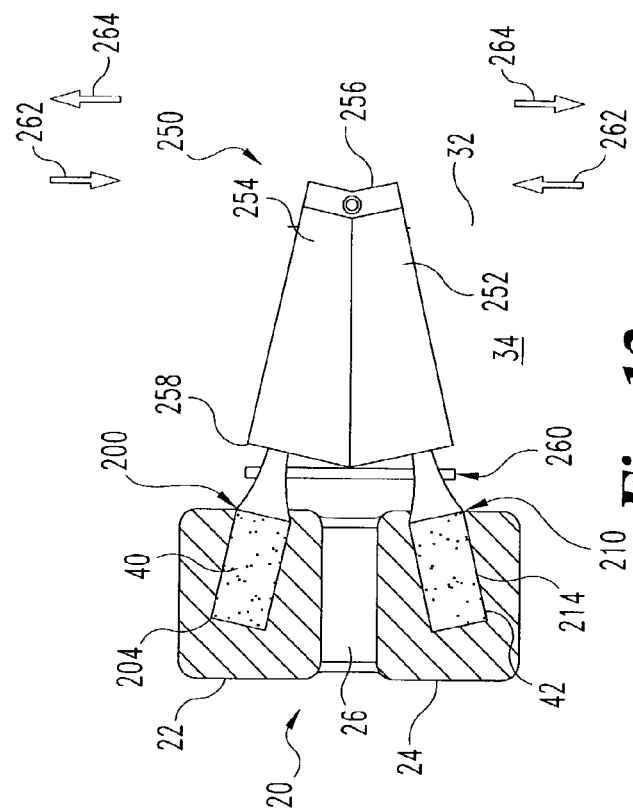
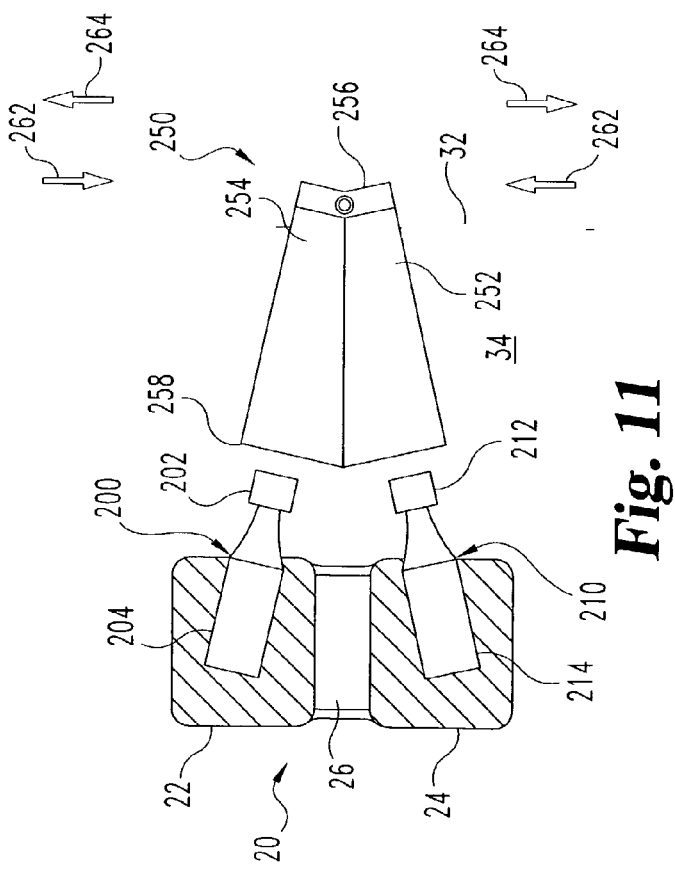

TECHNIQUES FOR SPINAL SURGERY AND ATTACHING CONSTRUCTS TO VERTEBRAL ELEMENTS

BACKGROUND

Several systems and devices are available to provide correction and stabilization of the spine. Such systems and devices can include screws engaged to the vertebral bodies and configured for engagement with elongated rods or plates that extend along the vertebral bodies. Devices for fusing adjacent vertebrae and artificial disc replacement are also available. Furthermore, nonoperative devices and methods, such as bracing and observation, can be used whenever applicable.

During a spinal surgical procedure, a device can be engaged to a vertebra and a load applied thereto to provide a corrective force. The corrective load that can be applied to the device can be limited by, for example, the ability of the device to receive the applied load and remain properly engaged to the bony structure in which it is implanted. In such cases the applied corrective load may cause movement of the device relative to the vertebra and the resulting loss of engagement or interface therebetween, or the corrective load may be limited to prevent such an occurrence.

There remains a need for spinal surgical techniques for attaching constructs to one or more vertebral elements that address these shortcomings in prior procedures.

SUMMARY

There is provided a surgical technique which includes a first surgical procedure for engaging a loading member to a bony portion, allowing the loading member to integrate with the bony portion, accessing the loading member in a second surgical procedure, and loading the integrated loading member.

There is further provided a surgical technique which includes a first surgical procedure for engaging first and second loading members to adjacent bony portions, allowing the first and second loading member to integrate with the respective bony portions, accessing the first and second loading members in a second surgical procedure, and attaching a construct to the integrated first and second loading members.

According to one aspect, there is provided a technique for spinal surgery that includes accessing at least one vertebral element in a first surgical procedure; engaging a loading member to the at least one vertebral element; allowing the loading member to integrate with the vertebral element; accessing the integrated loading member in a second surgical procedure; and applying a load to the integrated loading member.

According to another aspect, there is provided a technique for spinal surgery that includes accessing at least one vertebral element in a first surgical procedure; engaging a loading member to the at least one vertebral element; allowing the loading member to integrate with the vertebral element; accessing the integrated loading member in a second surgical procedure; and attaching a construct to the integrated loading member.

According to another aspect, there is provided a technique for spinal surgery that includes accessing at least one vertebral element in a first minimally invasive approach; engaging at least one loading member to the at least one vertebral element; allowing the at least one loading member to integrate with the bony structure of the vertebral element; accessing the at least one integrated loading member in a second minimally invasive approach; and applying a load to the at least one integrated loading member.

According to a further aspect, there is provided a technique for spinal surgery that includes accessing a first vertebral element in a first surgical procedure; engaging a first loading member to the first vertebral element; accessing a second vertebral element in the first surgical procedure; engaging a second loading member to the second vertebral element; allowing the first and second loading members to integrate with the first and second vertebral elements; accessing the integrated first and second loading members in a second surgical procedure; applying a load to the integrated first and second loading members; and attaching a construct to the integrated and loaded first and second loading members.

According to another aspect, a technique for spinal surgery is provided that includes accessing first and second vertebral elements of the spinal column in a first surgical procedure with at least one minimally invasive surgical approach to the first and second vertebral elements; engaging a first loading member to the first vertebral element; engaging a second loading member to the second vertebral element; allowing the first and second loading members to integrate with the bony structure of the respective first and second vertebral elements; accessing the integrated first and second loading members in a second surgical procedure; loading the integrated first and second loading members; and attaching a construct to the integrated first and second loading members.

According to a further aspect, there is provided a spinal surgical technique that includes accessing a number of vertebral elements in a first surgical procedure; engaging load receiving means to the number of vertebral elements; allowing the load receiving means to integrate with the number of vertebral elements; accessing the integrated loading receiving means in a second surgical procedure; loading the loading receiving means; and attaching a construct to the integrated and loaded load receiving means.

According to another aspect, a technique for spinal surgery is provided. The technique includes accessing first and second vertebral elements of the spinal column in a first surgical procedure with at least one minimally invasive surgical approach to the first and second vertebral elements; engaging a first loading member to the first vertebral element; engaging a second loading member to the second vertebral element; providing a temporary support between the first and second loading members; allowing the first and second loading members to integrate with the bony structure of the respective first and second vertebral elements; accessing the integrated first and second loading members in a second surgical procedure; and attaching a construct to the integrated first and second loading members.

These and other aspects will also be apparent from the following description.

BRIEF DESCRIPTION OF THE DRAWINGS

FIG. 5 is an elevational view in partial section showing intravertebral engagement of loading members to vertebrae of a spinal column segment in a minimally invasive procedure.

FIG. 6 is the view of FIG. 5 showing integrated loading members attached to a construct.

FIG. 11 is an elevational view in partial section showing intravertebral engagement of loading members to vertebrae of a spinal column segment in a minimally invasive procedure.

FIG. 12 is the view of FIG. 11 showing integrated loading members attached to a construct in a minimally invasive procedure.

DESCRIPTION OF THE ILLUSTRATED EMBODIMENTS

Figure 1:
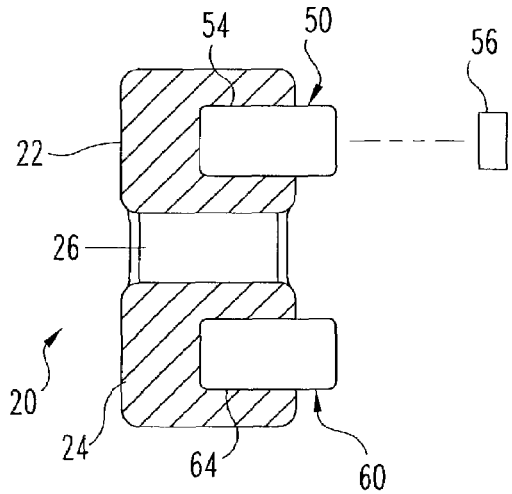
FIG. 1 is an elevational view in partial section showing intravertebral engagement of loading members to vertebrae of a spinal column segment.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein are contemplated as would normally occur to one skilled in the art to which the invention relates.

The present invention provides systems and techniques for correcting or treating spinal deformities and/or conditions. The systems and techniques include one or more loading members that can be engaged to one or more vertebral elements. The one or more loading members are allowed to integrate with the tissue of the one or more vertebral elements, and thereafter loaded and engaged to a construct. By applying the load to integrated loading members, the possibility of undesirable motion, loss of correction, or loss of fixation of the loading member with the vertebral element is minimized.

Referring to FIG. 1, there is shown a spinal column segment 20 in section including a first vertebral element 22 and a second vertebral element 24. First vertebral element 22 is spaced from second vertebral element 24 by a disc space 26. First vertebral element 22 and second vertebral element 24 are accessed in spinal surgery for engagement of a first loading member 50 to first vertebral element 22 and a second loading member 60 to second vertebral element 24. First loading member 50 includes a bone engagement portion 54 embeddable in or contactable with the bony structure of first vertebral element 22 to secure loading member 50 thereto. Second loading member 60 includes a bone engagement portion 64 embeddable in or contactable with the bony structure of second vertebral element 24 to secure second loading member 60 thereto.

It is contemplated that first loading member 50 and second loading member 60 can be configured to integrate with the bony structure of the respective first and second vertebral elements over time. For example, first and second loading members 50, 60 can be provided with any one or combination bone integration features along at least a portion of engagement portions 54, 64. Such bone integration features may include, for example, a hollow interior, one or more receptacles, one or more chambers, a porous coating, or exterior surface features. The integration features should allow bone to at least partially grow into, adhere to, attach, resorb and/or form with the engagement portions 54, 64 to integrate loading members 50, 60 to the bony and/or soft tissue structure of the respective vertebral elements 22, 24.

First and second loading members 50, 60 can also include bone growth material and/or bone growth facilitators. For example, a bone growth inducing material, such as a sponge, matrix, and/or other carrier impregnated with a protein such as BMP (bone morphogenic protein) and/or LMP (LIM mineralization protein) can be placed within, upon and/or around the loading members 50, 60. A cap or plug 56 can be provided, if necessary, and engaged to the loading members 50, 60 to retain bone growth material within the loading member to which it is engaged. Cap or plug 56 can be temporary or permanent. After engagement of loading members 50, 60 the access to the first and second vertebral elements can be surgically closed.

Figure 2:
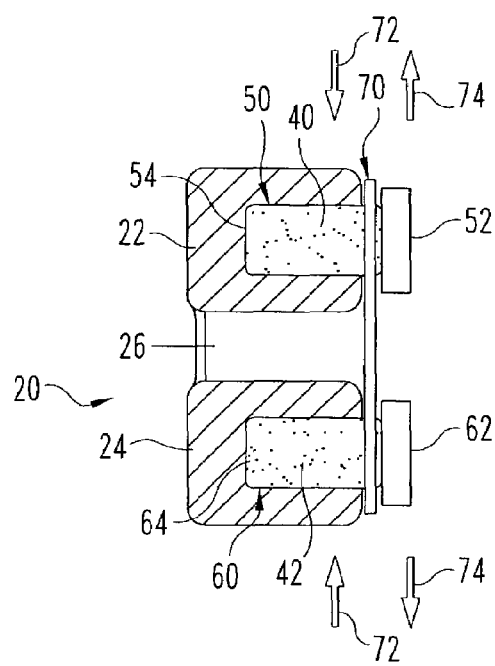
FIG. 2 is the view of FIG. 1 showing integrated loading members attached to a construct.

After integration has been obtained, loading members 50, 60 are accessed in a second surgical procedure for attachment of a construct 70 thereto. Construct 70 can extend between and interconnect the loading members, as shown in FIG. 2. In the illustrated embodiment, first loading member 50 is provided with a construct attachment portion 52, and second loading member 60 is provided with a construct attachment portion 62.

It is contemplated that the construct attachment portions discussed herein, such as attachment portion 52, 62, can be configured to attach by engaging, retaining, clamping, fastening, holding, contacting, securing or otherwise maintaining the construct to the respective loading member. The attachment portions can be separately attached to the loading members during the first surgical procedure or during the second surgical procedure. The attachment portions can be attached to the loading members after placement of the construct around a portion of the loading members extending from the vertebral elements. It is further contemplated that the construct can be supported entirely or partially by the attachment portions. It is also contemplated that the attachment portions could be integrally formed with the loading members.

For the second surgical procedure, it is contemplated that loading members 50, 60 will have integrated with the bony or tissue structure 40, 42 of vertebral elements 22, 24, and can have sufficient load carrying capabilities to withstand loading to correct or treat a spinal deformity or condition associated with spinal column segment 20. Various techniques are contemplated that can be employed to determine when and/or if integration has been achieved for performance of the second surgical procedure. Such techniques include, for example, awaiting the passage of a certain period of time, which can be based on known integration rates, experience, and/or anatomical studies. For example, it is contemplated that the passage of time may extend from a few weeks to several months before the second surgical procedure is performed. Integration of the loading members can also be based in whole or in part on the evaluation of radiographic, fluoroscopic or other imaging information taken of the loading members in situ.

The integrated loading members 50, 60 can be subjected to external loading in the second surgical procedure that can be greater than the loading that could applied pre-integration. Since integrated loading members 50, 60 can be subjected to higher initial loading, the desired surgical result may be achieved more efficiently and/or more effectively than if the loading members 50, 60 were loaded pre-integration. For example, in the second surgical procedure, compression loading 72 can be applied to the integrated loading members 50, 60, and construct 70 attached to the integrated, loaded loading members 50, 60. It is further contemplated that distraction loading 74 could be applied to the integrated loading members 50, 60, and construct 70 attached to the integrated, loaded loading members 50, 60. In either case, the loading is maintained with the attached construct 70 so that the desired surgical result can be achieved.

On specific application can be directed to the treatment of scoliosis. In such treatment, growth along the long or convex side of spine can be arrested by applying and maintaining a compression load between multiple loading members engaged to vertebral elements along the convex side of the spine. With integrated loading members, greater restraint to growth of the convex side of the spine can be provided, facilitating correction the scoliosis.

In another specific application, one or more interbody fusion devices can be inserted into disc space 26 in the second surgical procedure. A compression load can be applied to integrated loading members 50, 60 and maintained on the interbody fusion device(s) with construct 70 to facilitate fusion of the adjacent vertebral elements 22, 24. In a further specific application, disc space 26 can be collapsed, and a distraction load 74 applied directly to integrated loading members 50, 60 to restore the disc space height between vertebral elements 22, 24. The restored disc space height can be maintained by attaching construct 70 to the distracted, integrated loading members 50, 60.

It is further contemplated that more than one loading member can be provided in each vertebral element, and that more than two vertebral elements can be integrated with loading members. It is further contemplated that construct 70 can be configured for attachment with multiple loading members at each vertebral element, and can also be configured to extend along multiple vertebral elements, including three or more vertebral elements.

Figure 3:
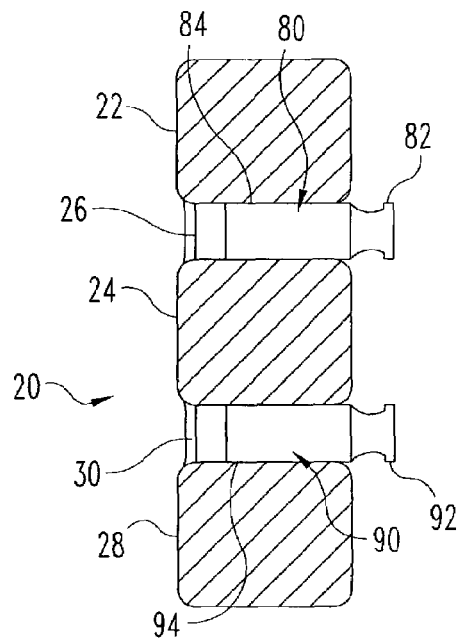
FIG. 3 is an elevational view in partial section showing intervertebral engagement of loading members to vertebrae of a spinal column segment.

Referring to FIG. 3, there is further shown spinal column segment 20 with a third vertebral element 28 and a disc space 30 between second vertebral element 24 and third vertebral element 28. First vertebral element 22 and second vertebral element 24 are accessed in a first surgical procedure for engagement of a first loading member 80 in disc space 26. Second vertebral element 24 and third vertebral element 28 are also accessed in a first surgical procedure for engagement of a second loading member 90 in disc space 30. First loading member 80 includes a bone engagement portion 84 embeddable in or contactable with the bony structure of first vertebral element 22 and second vertebral element 24 to secure loading member 80 thereto. Second loading member 90 includes a bone engagement portion 94 embeddable in or contactable with the bony structure of second vertebral element 24 and third vertebral element 28 to secure second loading member 90 thereto.

It is contemplated that first loading member 80 and second loading member 90 are configured to integrate with the bony structure of the respective vertebral elements over time. For example, first and second loading members 80, 90 can be provided with any one or combination bone integration features along at least a portion of engagement portions 84, 94. Such integration features may include, for example, a hollow interior, one or more receptacles, one or more chambers, a porous coating, or exterior surface features. The integration features allow bone to at least partially grow into, adhere to, attach, resorb and/or form with engagement portions 84, 94 to integrate loading members 80, 90 to the bony structure of the respective adjacent vertebral elements.

First and second loading members 80, 90 can also include bone growth material and/or bone growth facilitators. For example, a bone growth inducing material, such as a sponge, matrix, and/or other carrier impregnated with a protein such as BMP (bone morphogenic protein) and/or LMP (LIM mineralization protein) can be placed within, upon and/or around the loading members 80, 90. A temporary cap or plug can be provided, if necessary, and engaged to the loading members 80, 90 to retain bone growth material within the loading member during integration.

Figure 4:
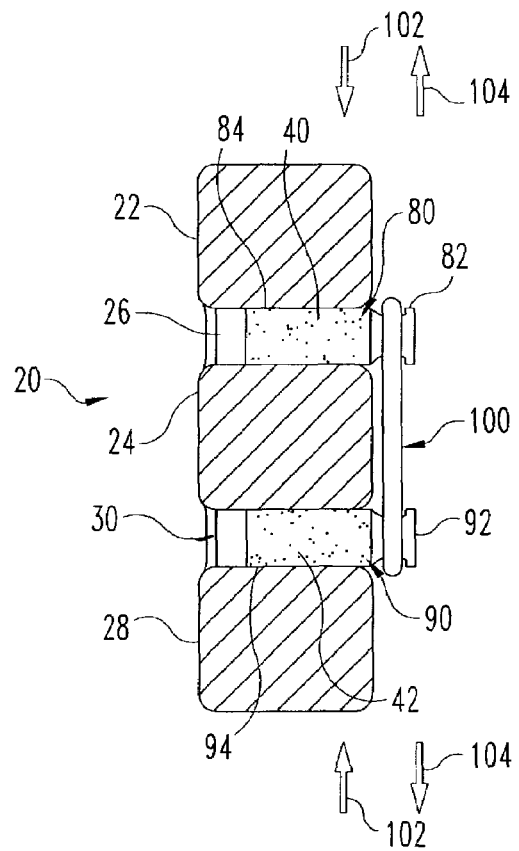
FIG. 4 is the view of FIG. 3 showing integrated loading members attached with a construct.

After integration has been obtained with the bony or tissue structure 40, 42, loading members 80, 90 are accessed in a second surgical procedure for attachment of a construct 100. Construct 100 can extend between and interconnect the loading members 80, 90, as shown in FIG. 4. It is contemplated that loading members 80, 90 will have integrated with the bony structure of the adjacent vertebral elements and will withstand loading to be applied thereto to correct or treat a spinal deformity or condition associated with spinal column segment 20. It is further contemplated that more than one loading member can be provided in each disc space, and that more than two vertebral levels can be integrated with loading members. It is further contemplated that construct 100 can be configured for attachment with multiple loading members at each vertebral level, and can also be configured to extend along multiple vertebral levels, including three or more vertebral levels.

In the illustrated embodiment, loading member 80 is provided with construct attachment portion 82 that can be attachable to or integrally formed with loading member 80. Attachment portion 82 can be attached to loading member 80 in either the initial insertion procedure of loading members 80, 90, or in the second procedure for loading loading members 80, 90 and attaching construct 100. Similarly, loading member 90 is provided with construct attachment portion 92 that can be attachable to or integrally formed with loading member 90. Attachment portion 92 can be attached to loading member 90 in either the initial insertion procedure or in the second procedure for loading loading members 80, 90 and attachment of construct 100.

The integrated loading members 80, 90 can be subjected to external loading in the second surgical procedure that can be greater than the loading that could applied pre-integration. Since integrated loading members 80, 90 can be subjected to higher initial loading, the desired surgical result may be achieved more efficiently and/or more effectively than if the loading members 80, 90 were loaded pre-integration. For example, in the second surgical procedure, compression loading 102 can be applied to the integrated loading members 80, 90, and construct 100 attached to the integrated and loaded loading members 80, 90. It is further contemplated that distraction loading 104 could be applied to the integrated loading members 80, 90, and construct 100 attached to the integrated and loaded loading members 80, 90.

For the loading members discussed herein, it is contemplated that the loading applied thereto can be any one or combination of compression loading, distraction loading, tension loading, torsional loading, and lateral loading. The loading can be applied with an instrument engageable to the integrated loading members and configured to apply the desired loading thereto in the second surgical procedure. For example, a distraction or compression instrument could be engaged to the integrated loading members, the desired loading applied to the integrated loading members, and the construct attached to the loaded, integrated loading members to post-operatively maintain all or a portion of the applied loading.

It is also contemplated that loading could be applied to the integrated loading members through the construct. For example, the construct could be tensioned and then attached to the integrated loading members in its tensioned state. The tensioned construct would apply a post-operative compression load between the integrated loading members. In another example, the construct could compressed, positioned between, and attached to the integrated loading members. The compressed construct would exert a post-operative distraction load between the loading members. In another example, the construct could be attached to the loading members, and configured or thereafter altered to apply a load to the loading members. The construct could be made from shape memory material, elastic material, or other material in which its properties, shape, form, size or other feature could be configured or altered to load the loading members.

Referring to FIG. 5 there is shown spinal column segment 20 with vertebrae 22, 24, 28 below skin 32 and tissue 34. Vertebrae 22, 24 and 28 can be accessed in a minimally invasive surgical approach for engagement of loading members 110, 120 and 130 thereto. For example, a retractor sleeve 170 can be inserted into a dilated path through skin 32 and tissue 34 to provide access therethrough to respective ones of the vertebrae 22, 24, 28. First loading member 110 is shown adjacent the proximal end of sleeve 170 before intravertebrally engaging engagement portion 114 to vertebra 22. Second and third loading members 120, 130 include engagement portions 124, 134, respectively, intravertebrally engaged with vertebrae 24, 28.

In one specific embodiment, loading members 110, 120, 130 are inserted in a minimally invasive surgical procedure such as can be performed with the METRx™ Surgical System marketed by Medtronic Sofamor Danek. Other minimally invasive surgical systems, procedures, and/or approaches for inserting the loading members and/or the constructs are also contemplated.

As shown in FIG. 6, loading members 110, 120, 130 have integrated with the bony structure 40, 42, 44 of vertebrae 22, 24 and 28, respectively. Loading members 110, 120, 130 are accessed in a second surgical procedure, and construct 140 can be attached to respective ones of the attachment portions 112, 122, 132 of loading members 110, 120, and 130. In one embodiment, attachment of construct 140 includes engaging coupling members 116, 126, 136 to respective ones of the attachment portions 112, 122, 132 to attach construct 140 thereto.

Various forms for the attachment portions discussed herein are contemplated. For example, with respect to attachment portions 112, 122, 132, there could include a threaded stem around with construct 140 can be placed, and coupling members 116, 126, 136 could be engaged to the threaded stem to attach construct 140 thereto. In another example, attachment portions 112, 122, 132 could include a passage sized to receive construct 140 therein, and coupling members 116, 126, 136 could be engaged to the respective attachment portions within or about the passage to attach construct 140 thereto. Coupling members 116, 126, 136 can be, for example, set screws, nuts, caps, clamps, wedges, retaining members or other devices capable of engaging either one or both of attachment portions 112, 122, 132 and construct 140 to attach construct 140 to loading members 110, 120, 130.

Figure 7:
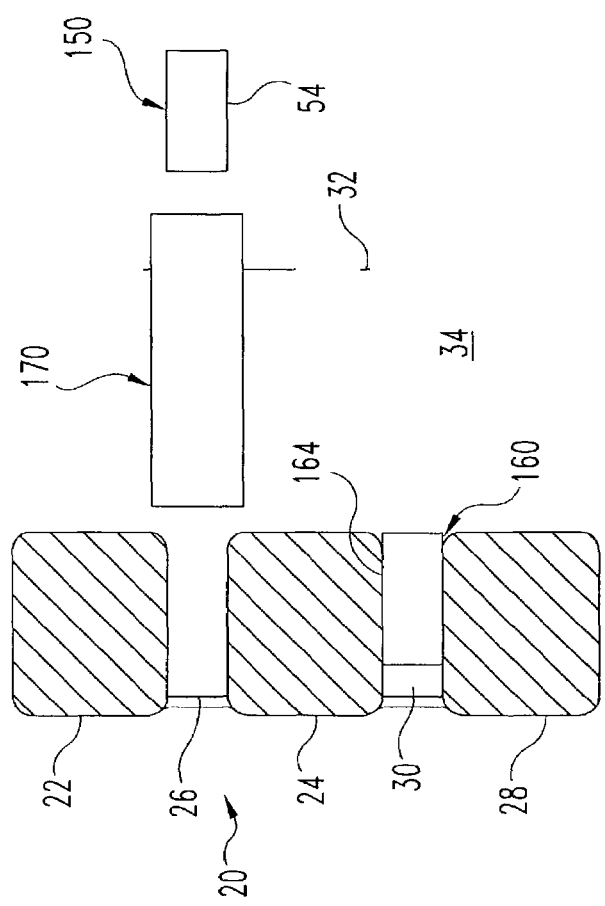
FIG. 7 is an elevational view in partial section showing intervertebral engagement of loading members to vertebrae of a spinal column segment in a minimally invasive procedure.

Referring to FIG. 7 there is shown spinal column segment 20 with vertebrae 22, 24, 28 below skin 32 and tissue 34. The disc spaces 26, 30 between adjacent ones of vertebrae 22, 24 and 28 can be accessed in a minimally invasive surgical approach for engagement of loading members 150, 160 thereto. For example, retractor sleeve 170 can be inserted into a dilated path through skin 32 and tissue 34 to provide access therethrough to respective ones of the disc spaces 26, 30. First loading member 150 is shown adjacent the proximal end of sleeve 170 before intervertebrally engaging engagement portion 154 of loading member 150 with vertebrae 22, 24 in disc space 26. Second loading member 160 includes engagement portion 164 intervertebrally engaged with vertebrae 24, 28 in disc space 30.

The vertebrae can be prepared to receive the loading member to be engaged thereto by removing or cutting material, reaming, drilling, and/or tapping holes or receptacles in the bony structure or soft tissue structure of the vertebrae. In one specific embodiment, loading members 150, 160 are inserted in a minimally invasive surgical procedure such as can be performed with the METRx™ Surgical System marketed by Medtronic Sofamor Danek. Other minimally invasive surgical systems, procedures, and/or approaches for inserting the loading members and/or the constructs are also contemplated.

Figure 8:
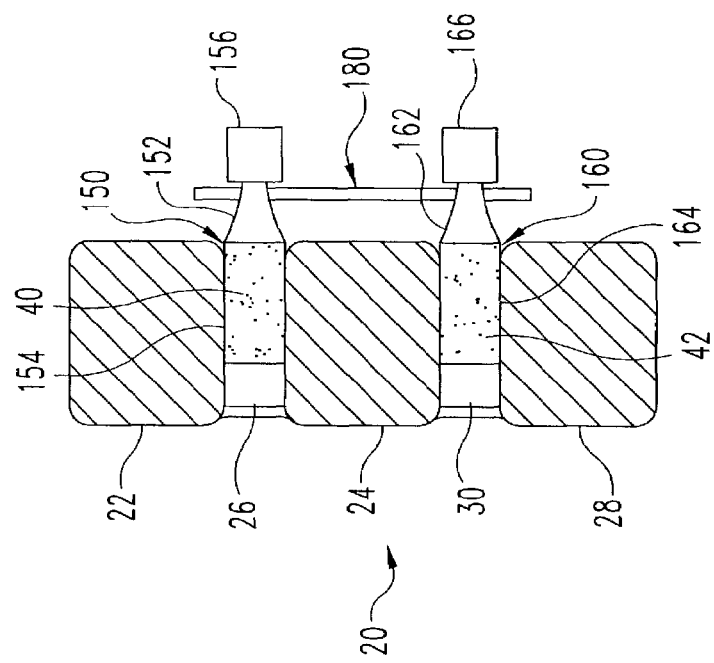
FIG. 8 is the view of FIG. 7 showing integrated loading members attached to a construct.

As shown in FIG. 8, loading members 150, 160 have integrated with the bony structure 40, 42 between vertebrae 22 and 24 and between vertebrae 24 and 28, respectively. Loading members 150, 160 are accessed in a second surgical procedure, and construct 180 is attached to respective ones of the attachment portions 152, 162 of loading members 150, 160. As discussed above with respect to coupling members 116, 126, 136, coupling members 156, 166 can be coupled to respective ones of the attachment portions 152, 162 to secure construct 180 to the loading members.

In minimally invasive approaches employing a micro-incision or sleeve, such as retractor sleeve 170, viewing of the spinal column segment can be performed by any one or combination of placing an endoscope through the incision or sleeve, microscopically viewing the surgical site through incisions or the sleeve, endoscopically or microscopically viewing the surgical site through a second portal to the spinal column segment, and through imaging systems, including fluoroscopic, radiographic, and stereotactic systems.

Figure 9:
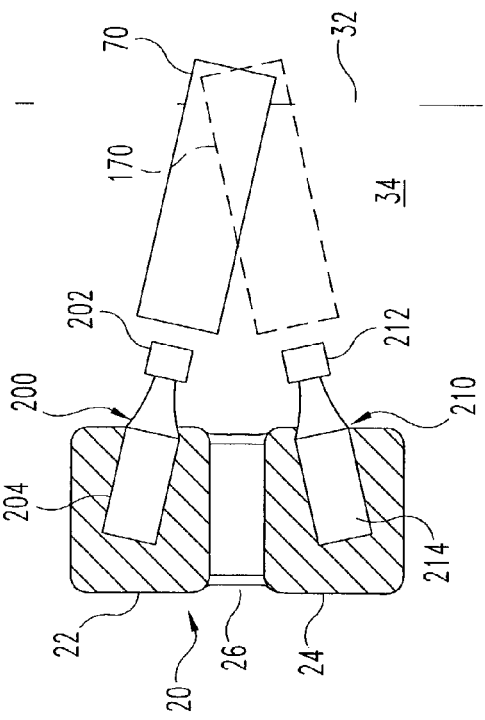
FIG. 9 is an elevational view in partial section showing intravertebral engagement of loading members to vertebrae of a spinal column segment in a minimally invasive procedure.

Referring to FIG. 9 there is shown spinal column segment 20 with vertebrae 22, 24 below skin 32 and tissue 34. Each of the vertebrae 22, 24 can be accessed in a minimally invasive surgical approach for engagement of loading members 200, 210 thereto. For example, retractor sleeve 170 can be inserted into a dilated path through skin 32 and tissue 34 to provide access therethrough to each of the vertebrae 22, 24 through a single sleeve. First loading member 200 includes an engagement portion 204 and can be engaged to vertebra 22 through sleeve 170. Sleeve 170 can be repositioned through skin 32 and tissue 34, as shown in dashed lines, for access to vertebra 24. Second loading member 210 includes engagement portion 214 that can be engaged to vertebra 24.

Figure 10:
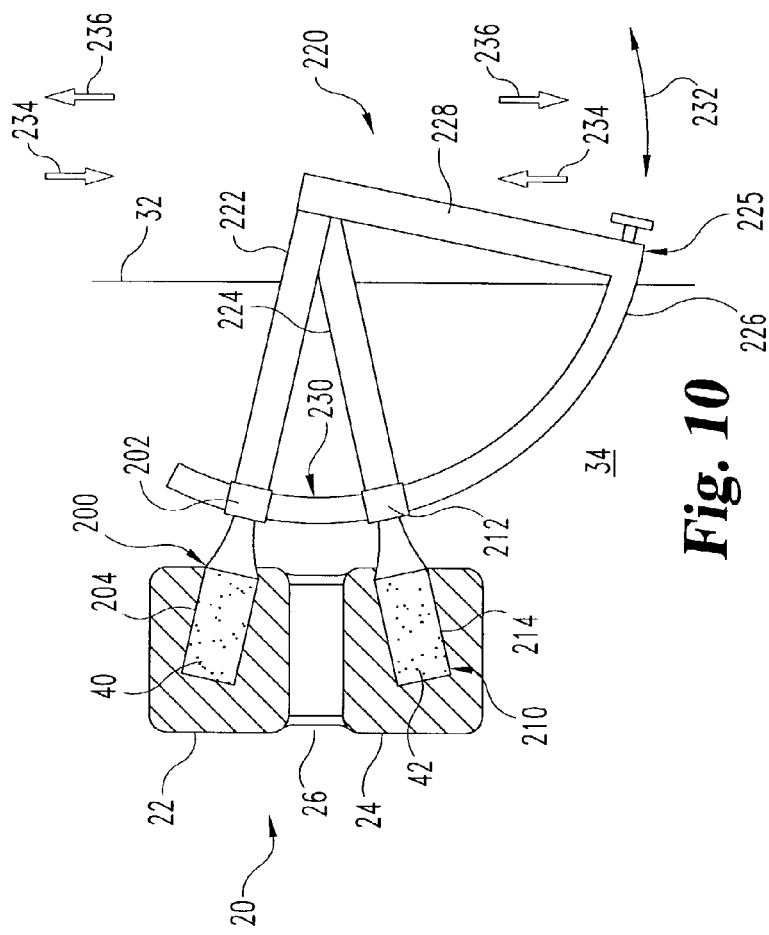
FIG. 10 is the view of FIG. 9 showing integrated loading members attached to a construct in a minimally invasive procedure.

As shown in FIG. 10, loading members 200, 210 have integrated with the bony structure 40, 42 of vertebrae 22, 24, respectively. Loading members 200, 210 are accessed in a second surgical procedure, and construct 230 is attached to respective ones of the attachment portions 202, 212 of loading members 200, 210. Coupling members or the like can be engaged to loading members 200, 210 and/or attached to construct 230 to attach construct 230 to the integrated loading members 200, 210.

In FIG. 10, construct 230 is mounted to a minimally invasive construct insertion instrument, such as the SEXTANT™ Percutaneous Spinal System marketed by Medtronic Sofamor Danek. Instrument 220 includes a first extension 222 coupled to first loading member 200 and a second extension 224 coupled to second loading member 210. Extensions 222, 224 can be percutaneously guided for coupling with the respective loading member, positioned through a retractor sleeve aligned with the respective ones of loading members 200, 210, or the surgical site can be opened and retracted for insertion and coupling of the extensions to integrated loading members 200, 210. A construct inserter 225 is pivotally mounted to the extensions 222, 224. Construct inserter 225 includes a body 228 and an arm 226 extending from body 228. Arm 226 can be curved to follow an arc 232 along which construct 230 is swung by pivoting inserter 225 about the extensions 222, 224. Construct 230 can be a rod, tether, plate or other element configured to extend between and interconnect loading members 200, 210.

To insert construct 230, inserter 225 is pivoted along path 232 to percutaneously introduce construct 230. Inserter 225 is further pivoted to advance construct 230 to a location adjacent loading members 200, 210. Loading members 200, 210 can be provided with attachment portions 202, 212 adapted to receive construct 230, or around which construct 230 can be positioned, or that construct 230 can be positioned adjacent to. For example, attachment portions 202, 212 can be in the form of a head of a multi-axial screw with a passage sized to receive construct 230 and internally threaded to receive a set screw to attach construct 230 in the head, such as is provided with the M8™ multi-axial screw marketed by Medtronic Sofamor Danek.

Before or after introduction of construct 230, loading members 200, 210 can be loaded through extensions 222, 224. For example, a compression load 234 or distraction load 236 can be applied to extensions 222, 224 coupled to loading members 200, 210. Construct 230 can then be inserted, if not already inserted, and attached to each of the loading members 200, 210 while the loading members are maintained in their loaded condition.

Referring to FIG. 11 there is shown spinal column segment 20 with vertebrae 22, 24 below skin 32 and tissue 34. Each of the vertebrae 22, 24 can be accessed in a minimally invasive surgical approach for engagement of loading members 200, 210 thereto. For example, retractor 250 can be inserted through skin 32 and tissue 34 to provide access therethrough to each of the vertebrae 22, 24. Retractor 250 can include first and second portions 252, 254 having a reduced size configuration for insertion of retractor 250, and portions 252, 254 can be expanded or moved away from one another after insertion to provide access to each of the vertebrae 22, 24 through an enlarged working channel.

As shown in FIG. 12, loading members 200, 210 have integrated with the bony structure 40, 42 of vertebrae 22, 24, respectively. Loading members 200, 210 are accessed in a second surgical procedure, and construct 260 is attached to respective ones of the attachment portions 202, 212 of loading members 200, 210. Retractor 250 could be employed and expanded to simultaneously access integrated loading members 200, 210. Coupling members or the like can be coupled to attachment portions 202, 212 and/or to construct 260 to attach construct 260 to loading members 200, 210.

Before or after introduction of construct 260 through retractor 250, integrated loading members 200, 210 can be loaded through extensions coupled thereto, through an instrument coupled to loading members 200, 210, or through construct 260. For example, a compression load 262 or distraction load 264 can be applied to the integrated loading members 200, 210. Construct 260 can then be inserted and/or engaged to each of the loading members 200, 210 while the loading members are maintained in their loaded condition.

Other minimally invasive access instruments are contemplated. In the embodiment illustrated in FIGS. 11 and 12, retractor 250 includes first and second portions 252, 254 pivotally coupled at proximal end 256 to increase the size of distal end 258 to access each of the vertebrae 22, 24. Other examples include inflatable or resiliently expandable retractors, or retractors having first and second portions, or additional portions, mounted at their proximal ends to a linkage mechanism and movable along the linkage mechanism to retract tissue to access the surgical site.

Figure 13:
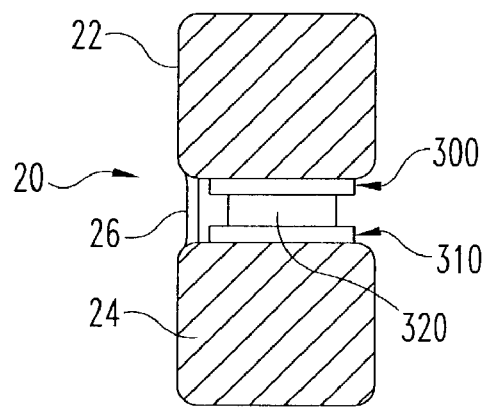
FIG. 13 is an elevational view in partial section showing intervertebral engagement of loading members to vertebrae of a spinal column segment in a minimally invasive procedure.

Referring to FIG. 13 there is shown spinal column segment 20 with vertebrae 22, 24. Each of the vertebrae 22, 24 can be accessed in a minimally invasive or open surgical approach for engagement of loading members 300, 310 thereto. Loading member 300 is positioned adjacent to or in engagement with the endplate of upper vertebra 22 in disc space 26, and loading member 310 is positioned adjacent to or in engagement with the endplate of lower vertebra 24 in disc space 26. Vertebrae 22, 24 can be distracted, if necessary to provide a sufficient disc space height between vertebrae 22, 24 for positioning of loading members 300, 310 therein. To prevent disc space 26 from collapsing, a temporary spacer 320 can be positioned between loading members 300, 310.

Figure 14:
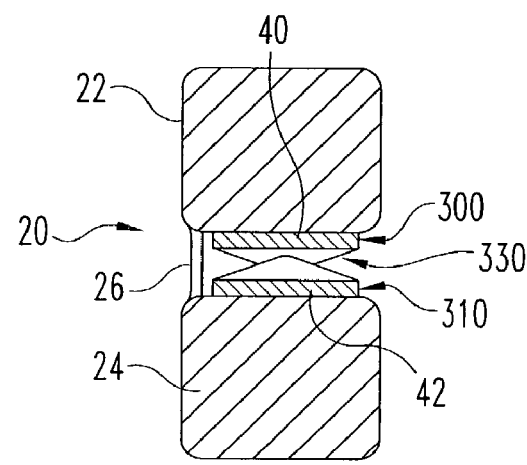
FIG. 14 is the view of FIG. 13 showing integrated loading members attached to a construct positioned therebetween.

As shown in FIG. 14, loading members 300, 310 have been allowed to integrate with the bony structure 40, 42 of vertebrae 22, 24, respectively, while temporary spacer 320 prevent the disc space from collapsing. Loading members 300, 310 are accessed in a second surgical procedure, and temporary spacer 320 removed. A distraction load can then be applied to directly to loading members 300, 310, or directly to the vertebral bodies 22, 24, to provide a desired disc space height between vertebrae 22, 24. Construct 330 can then be positioned between loading members 300, 310 to maintain disc space 26 at the desired disc space height. With construct 330 positioned therebetween, integrated loading members 300, 310 are subjected to the loading necessary to maintain disc space 26 at the desired disc space height with construct 330. The potential for subsidence into the adjacent vertebrae and/or movement of loading members 300, 310 along the adjacent endplate is reduced or eliminated since loading members 300, 310 have integrated with the adjacent vertebrae 22, 24

In the embodiment of FIGS. 13, 14, loading members 300, 310 can be plate-like elements positioned along the endplates of vertebrae 22, 24. Loading members 300, 310 can include spikes, projections, bone screws, anchors, ridges, teeth, holes, or other features that extend into the respective adjacent vertebrae 22, 24, and/or be made from material which integrates with the endplates of vertebrae 22, 24. Loading members 300, 310 can provide endplate replacement or reconstruction for subsequent loading of the vertebrae after integration of loading members 300, 310. Loading members 300, 310 can also be L-shaped and have a portion (not shown) extending along the exterior surface of the respective adjacent vertebra in addition to the portion of the loading member positioned along the endplate of the adjacent vertebra.

Temporary spacer 320 can be a block of material positioned between loading members 300, 310 having sufficient rigidity to prevent disc space 26 from collapsing beyond desired limits. Temporary spacer 320 can be attached to loading members 300, 310 with screws, anchors, an interface between the components, or other arrangement permitting subsequent removal of temporary spacer 320.

Construct 330 can be an articulating disc, artificial disc, artificial nucleus or other interbody device capable of maintaining the restored the disc space height and preserving segmental motion. Construct 330 can be comprised of material including any one or combination of characteristics, including inflatable, flowable, hydratable, expandable, compressible, and/or elastic material. Construct 330 could also be a distraction spacer inserted between integrated loading members 300, 310 to restore the disc space height by separating loading members 300, 310 and thus vertebrae 22, 24. Construct 330 could also be positioned in an already distracted disc space between loading members 300, 310. Construct 330 could be configured and/or be comprised of material that permits bony fusion between vertebrae 22, 24.

As discussed herein, the loading members can be engaged intervertebrally or intravertebrally to the one or more vertebral elements. It is contemplated that loading members can be engaged intervertebrally and intravertebrally with vertebral elements in the same surgical procedure. The loading members can include any one or combination of features to integrate the loading member with tissue structure of the vertebral elements. The loading members can include material therein and/or incorporated therewith to promote or accelerate bone growth. The loading members can provide solid bony attachment to or between vertebral elements of the spinal column segment. The loading members have application in, for example, the correction of spinal deformities; the temporary or permanent stabilization of a segment of the spinal column; the temporary or permanent rigid fixation of bone; the temporary or permanent flexible fixation of bone; as a buttress for bone grafts, artificial discs or fusion devices for the spine; for application and maintenance of a compression load or distraction load on a spinal column segment; and/or for fusionless scoliosis surgery, for example.

The vertebral elements can be an anterior portion of a vertebral body, the endplates of a vertebral body or of adjacent vertebral bodies, or any of the posterior elements of the vertebral body, including the facets, pedicle, and spinous or transverse processes. The vertebral elements can also be tissue elements associated with the vertebral bodies, such as annulus tissue or ligament tissue.

The loading members can be provided in the form of a screw, bolt, staple, wedge, spike, spacer, cage, anchor, hollow body, solid body, plate, or other form. The loading members can be provided with a bone engagement portion positionable in the vertebral element or between vertebral elements for integration with the bony structure. The bone engagement portion of the loading members can include threads, no threads, smooth surfaces, splines, teeth, nubs, knurlings, spikes, barbs, or other bone engaging projections therealong to engage the adjacent bony tissue. The bone engagement portion of the loading members can have an overall shape that is any one or combination of cylindrical; frusto-conical; tapered; cuboid; rectangular; plate-like shape with convex surfaces, concave surfaces, and/or L-shaped; or any other overall shape suitable for a loading member. The bone engagement portion of the loading members can have a cross-sectional shape that is polygonal, square, rectangular, circular, oval, elliptical, multiple curved and linear segments or any other cross-sectional shape suitable for a loading member. The bone engagement portion of the loading members can be hollow or solid, and provided with any one or combination of fenestration openings, cannulations, multiple chambers, recesses, cavities, pits, receptacles or the like to receive bone growth.

The loading members can be provided with a configuration suitable for attachment of a construct, or for attachment to a device to which a construct is engaged. For example, the loading members can be integrally formed with an attachment portion to which the construct is engaged. The loading members can also have an attachment portion coupled thereto by, for example, internally threading the attachment portion to the loading member; externally threading the attachment portion to the loading member; clipping, clamping, interlocking, slidingly receiving, frictionally fitting, welding, gluing, bayonet locking, or otherwise securing the attachment portion to the loading member. The loading members can be provided with an attachment portion configured for engagement with an insertion instrument, or configured for engagement with an instrument for driving the loading member into engagement with the vertebral element. The loading members could also be configured so that the proximal end of the bone engagement portion could be engaged by an insertion tool.

The attachment portion of the loading members can be configured so that the construct could be placed over, around, within, between, along, and/or through the attachment portion. Coupling members can be used coupled to the construct to the attachment portion. The attachment portions could also be configured to attach to one or both of the loading member and the construct after the construct has been placed adjacent to or secured to the loading member.

The loading members can be fabricated in whole or in part from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials include carbon-reinforced polymer composites, shape-memory alloys, titanium, titanium alloys, cobalt chrome alloys, stainless steel, ceramics and combinations thereof.

Constructs can be used to treat a spinal deformity or condition by attaching at least one construct to one or more integrated loading members subjected to loading conditions. A wide variety of surgical approaches and techniques are contemplated for accessing the spinal column to engage loading members to vertebral elements, and for attaching and loading the integrated loading members. Such techniques include open surgical techniques in which skin and tissue are retracted to expose the spinal column, and minimally invasive surgical techniques. The surgical approach to the spinal column segment may also be any one or combination of anterior, lateral, posterior, postero-lateral, or antero-lateral approaches. The surgical approaches may employ open, endoscopic, laparoscopic, thorascopic, microscopic, and surgical navigation procedures and combinations thereof. The approaches may be made to any portion of the spinal column, including the cervical, thoracic, lumbar and sacral regions of the spine.

The loading members described herein can be used for the correction or treatment of a spinal deformity or condition through attachment of a construct to one or more vertebral elements along the affected segment of the spinal column. It is contemplated that, after the loading members have integrated with the vertebral elements, the loading members can be accessed in a second surgical procedure, subjected to the desired loading, and attached to the one or more constructs. It is contemplated that such constructs can include tethering constructs, plate constructs, rod constructs, and/or artificial disc constructs extending between one or more vertebral elements. Further examples of constructs include, but are not limited to, staples, cables, artificial strands, rods, plates, springs, artificial ligaments, articulating components, artificial disc material components, hydrogel components, artificial nucleus components, and combinations thereof. The constructs can be rigid, semi-rigid, flexible, partially flexible, resorbable, non-resorbable, superelastic, or include shape-memory material. Further examples of tether constructs include those that are single strand, multiple strands, braided, or combinations thereof. Tether material can include but is not limited to polymers, such as polyester and polyethylene; superelastic metals, such as nitinol; shape memory alloy, such as nickel titanium; resorbable synthetic materials, such as suture material; metals, such as stainless steel and titanium; synthetic materials, allograft material; and bioelastomer material.

Aspects of the present invention also have application in correction of non-spinal deformities or conditions, such as joint replacement or reconstruction. In such techniques, loading members can be positioned in adjacent bony portions in a first surgical procedure. The loading members are allowed to integrate with respective bony portions. The integrated loading members are accessed in a second surgical procedure and subjected to loading to correct a deformity or condition associated with the adjacent bony portions. A construct can be attached to the integrated loading members to maintain or apply corrective loading. It is further contemplated that a construct configured to restore or provide motion between the adjacent bony portions could be attached to the integrated loading members. Examples of such joint replacement techniques include hip, knee, wrist, ankle, shoulder, elbow, ankle, finger and temporomandibular joint applications.

While the invention has been illustrated and described in detail in the drawings and foregoing description, the same is to be considered illustrative and not restrictive in character. All changes and modifications that come within the spirit of the invention are desired to be protected.

What is claimed is:

1. A technique for spinal surgery, comprising:
   accessing at least one vertebral element in a first surgical procedure;
   engaging a loading member to the at least one vertebral element;
   allowing the loading member to integrate with the vertebral element in a substantially unloaded condition;
   accessing the integrated loading member in a second surgical procedure; and
   applying a load to the integrated loading member.

2. The technique of claim 1, wherein the load is a compression load.

3. The technique of claim 1, wherein the load is a distraction load.

4. The technique of claim 1, wherein the loading member integrates with the bony structure of the at least one vertebral element in a substantially unloaded condition.

5. The technique of claim 1, wherein the loading member is an intravertebral loading member engageable to the at least one vertebral element.

6. The technique of claim 5, wherein the loading member includes bone growth facilitating material.

7. The technique of claim 1, wherein the loading member is engaged to the at least one vertebral element from a posterior approach.

8. The technique of claim 1, wherein the loading member is engaged to the at least one vertebral element from an anterior approach.

9. The technique of claim 1, wherein the loading member is engaged to the at least one vertebral element from a lateral approach.

10. The technique of claim 1, wherein accessing the at least one vertebral element includes accessing the at least one vertebral element in a minimally invasive approach.

11. The technique of claim 10, wherein accessing the integrated loading member includes accessing the integrated loading member in an open surgical approach.

12. The technique of claim 10, wherein accessing the integrated loading member includes accessing the integrated loading member in a minimally invasive approach.

13. The technique of claim 1, further comprising attaching a construct to the integrated loading member.

14. The technique of claim 13, wherein the construct is selected from the group consisting of: a plate, a tether, and a rod.

15. The technique of claim 1, further comprising:
   accessing a second vertebral element in a second surgical procedure;
   engaging a second loading member to the second vertebral element;
   allowing the second loading member to integrate with the second vertebral element;
   accessing the integrated second loading member in the second surgical procedure; and
   applying a load to the integrated second loading member.

16. The technique of claim 15, further comprising attaching a construct to each of the integrated loading members in the second surgical procedure.

17. The technique of claim 16, wherein the construct is selected from the group consisting of: a plate, a tether, and a rod.

18. The technique of claim 16, wherein applying the load to the integrated loading member and the integrated second loading member includes tensioning the construct and attaching the tensioned construct to each of the integrated loading members.

19. The technique of claim 16, wherein applying the load to the integrated loading member and the integrated second loading member includes compressing the construct and attaching the compressed construct to each of the integrated loading members.

20. The technique of claim 16, wherein the construct is inserted in a minimally invasive approach.

21. The technique of claim 15, wherein applying the load to the integrated loading member and the integrated second loading member includes applying a compression load to the integrated loading members.

22. The technique of claim 21, further comprising attaching a construct to each of the integrated loading members with the compression load applied therebetween.

23. The technique of claim 15, wherein applying the load to the integrated loading member and the integrated second loading member includes applying a distraction load to the integrated loading members.

24. The technique of claim 23, further comprising attaching a construct to each of the integrated loading members with the distraction load applied therebetween.

25. The technique of claim 1, wherein the loading member includes one or more integration features selected from the group consisting of: a porous coating, a hollow interior, one more chambers, one or more surface features, and one or more receptacles.

26. The technique of claim 1, wherein the loading member includes an engagement portion engageable with the at least one vertebral element and an attachment portion extending from the engagement portion for attachment of a construct thereto.

27. The technique of claim 26, wherein the attachment portion is integrally formed with the engagement portion.

28. The technique of claim 1, further comprising inserting a device in a spinal disc space adjacent the at least one vertebral element in the second surgical procedure.

29. The technique of claim 1, wherein the first surgical procedure is completed at least two months prior to the second surgical procedure.

30. A technique for spinal surgery, comprising:
accessing a first vertebral element in a first surgical procedure;
engaging a first loading member to the first vertebral element;
accessing a second vertebral element in the first surgical procedure;
engaging a second loading member to the second vertebral element;
allowing the first and second loading members to integrate with the first and second vertebral elements;
accessing the integrated first and second loading members in a second surgical procedure;
applying a load to the integrated first and second loading members; and
attaching a construct to the integrated and loaded first and second loading members.

31. The technique of claim 30, wherein the first surgical procedure includes a single minimally invasive approach to each of the vertebral elements.

32. The technique of claim 30, wherein the first surgical procedure includes a first minimally invasive approach to the first vertebral element and a second minimally invasive approach to the second vertebral element.

33. The technique of claim 30, wherein the construct is inserted in a minimally invasive approach to engage the construct to the integrated and loaded first and second loading members.

34. The technique of claim 30, wherein the load is applied to the integrated first and second loading members in a minimally invasive approach.

35. The technique of claim 34, wherein the minimally invasive approach includes coupling first and second extensions to respective ones of the integrated loading members and applying the load to each of the integrated loading members includes applying the load through the extensions.

36. The technique of claim 35, further comprising mounting a construct insertion instrument to each of the extensions and percutaneously inserting the construct for attachment with each of the integrated and loaded first and second loading members.

37. The technique of claim 30, wherein the construct is inserted in a minimally invasive approach and engaged to the integrated and loaded loading members.

38. The technique of claim 30, wherein the loading members are engaged intravertebrally with respective ones of the vertebral elements.

39. A spinal surgical technique, comprising:
accessing a number of vertebral elements in a first surgical procedure;
engaging load receiving means to each of the number of vertebral elements;
allowing each of the load receiving means to integrate with the number of vertebral elements in a substantially unloaded condition;
accessing the integrated loading receiving means in a second surgical procedure; loading the loading receiving means; and
attaching a construct to the integrated load receiving means.

40. The technique of claim 39, wherein the load receiving means includes a number of intravertebral loading members.

41. The technique of claim 39, wherein the load receiving means is integrated with bony structure of the vertebral elements.

42. The technique of claim 39, wherein the load receiving means includes means for attaching the construct thereto.

43. The technique of claim 39, wherein each of the number of vertebral elements is accessed in a minimally invasive approach.

* * * * *